United States Patent [19]

Recker

[11] Patent Number: 5,164,368

[45] Date of Patent: Nov. 17, 1992

[54] TREATMENT FOR OSTEOPOROSIS USING GROWTH HORMONE RELEASING FACTOR (GRF) IN COMBINATION WITH PARATHYROID HORMONE (PTH)

[76] Inventor: Robert R. Recker, 3309 S. 116th St., Omaha, Nebr. 68144

[21] Appl. No.: 787,051

[22] Filed: Nov. 4, 1991

Related U.S. Application Data

[63] Continuation of Ser. No. 617,543, Nov. 26, 1990, abandoned.

[51] Int. Cl.$^5$ .............................................. A61K 37/36
[52] U.S. Cl. .......................................... 514/12; 514/2; 514/21
[58] Field of Search ................................ 514/12, 21, 2

[56] References Cited

U.S. PATENT DOCUMENTS 4,710,382 12/1987 Recker ................................. 514/2 X
4,870,054 9/1989 Recker ................................. 514/12

OTHER PUBLICATIONS

Reeve et al, Osteoporosis Int (1991), 162–170.
Neer et al. Osteoporosis (1987), 829–835.
Reeve et al. Br. med. J. (1980), 280–1340–4.

Primary Examiner—Howard E. Schain
Attorney, Agent, or Firm—Zarley, McKee, Thomte, Voorhees & Sease

[57] ABSTRACT

A method of treating osteoporosis, especially postmenopausal osteoporosis, by administering on a periodic but regular basis to a patient growth hormone releasing factor, GRF(1–44)-NH$_2$, or a biologically active analog thereof, and concurrently administering parathyroid hormone, PTH(1–34)-NH$_2$ and continuing the administration until bone mass increases and the patient's calcium balance becomes positive and indicates a mineral accumulation in the skeleton.

17 Claims, No Drawings

TREATMENT FOR OSTEOPOROSIS USING GROWTH HORMONE RELEASING FACTOR (GRF) IN COMBINATION WITH PARATHYROID HORMONE (PTH)

This is a continuation of copending application Ser. No. 07/617,543 filed on Nov. 26, 1990, now abandoned.

BACKGROUND OF THE INVENTION

In the past 20 years, the physiology of pituitary function has become better understood. The pituitary gland secretes several hormones which in turn control secretion of other glands such as the adrenal, the thyroid, and the reproductive organs. In recent times, a series of pituitary releasing hormones have been discovered, and characterized. The most recent of these is growth hormone releasing factor $GRF(1-44)-NH_2$. This discovery occurred in 1982 when two investigators independently, but almost simultaneously, reported the presence of a substance occurring in a pancreatic tumor which caused a clinical syndrome called acromegaly. In their respective journal articles, they reported that the tumors were found to contain a peptide consisting of 44 amino acids, which when purified and injected into animals or humans was found to stimulate growth hormone production intensively, *Science*, Vol. 218, Nov. 5, 1982. pp. 585-87 and *Nature*, Vol. 300, Nov. 18, 1982, pp. 276-78. Recently, some researchers have successfully, synthetically synthesized growth hormone releasing factor, and very recently it has been produced by genetic engineering procedures using bacterial cultures. For literature relating to synthetic production of growth hormone releasing factor, see Gelato, M. C. et al., 1983, "The Effects of Growth Hormone Releasing Factor in Man," *Journal of Clinical Endrocrinology and Metab.*, 57674.

Growth hormone releasing hormone factor is a peptide of 44 amino acids. There are analogs containing 27-40 amino acids. It is one of a group of peptides secreted by the hypothalamus, and it normally stimulates pituitary growth hormone release. It is important in normal growth and development during childhood.

Recently, it has been reported that $GRF(1-44)-NH_2$ may have some promise in the treatment of growth hormone deficiency (see *Journal of Clinical Endrocrinoloqy and Metab.*, 59:1, 1984 and *Journal of Clinical Endrocrinoloqy and Metab.*, 58:1043, 1984). However, $GRF(1-44)-NH_2$ has not been marketed or suggested for any specific clinical disease treatment. It has been suggested as likely to be useful for testing pituitary function by using doses to stimulate pituitary secretion of growth hormone. The theory being that in the event it does not so stimulate, one knows that the pituitary gland is not functioning properly. However, when used to test pituitary function, $GRF(1-44)-NH_2$ is administered intravenously by a single bolus injection and blood levels of growth hormone are measured in serum specimens obtained at approximately half hour intervals for four hours. If growth hormone levels fail to rise, then the presumption is made that the pituitary gland is incapable of secreting growth hormone. This is a single dose for diagnostic purposes, not a periodic and regular treatment pattern.

Postmenopausal osteoporosis is defined as the presence of severe loss of bone, with or without fractures, in women who are past menopause. Bone loss without fractures has been termed osteopenia, although many refer to bone loss with or without fractures as osteoporosis. The bone loss is from the "inside" of the skeleton rather than a shrinkage of the outer volume of the skeleton. The skeleton "hollows out." For many years, physicians have been searching for an agent that will cause reaccumulation of this lost bone so that risk of fracture is diminished. It is a major public health problem affecting millions of postmenopausal women. Almost half of the Caucasian women in the United States can be expected to suffer fractures from osteoporosis before they die.

The invention of my two prior patents dealt with the treatment of osteoporosis, preferably postmenopausal osteoporosis with $GRF(1-44)-NH_2$ until the patient's bone mass increases and the patient's calcium balance becomes positive, indicating mineral accumulation in the skeleton, see Recker U.S. Pat. Nos. 4,710,382 issued Dec. 1, 1987 and U.S. Pat. No. 4,870,054, issued Sep. 26, 1989.

One particular problem with postmenopausal females is that the loss of skeletal mass is most heavy in the hip and spine. Thus, with a process such as that described in my previous two patents, while such is extremely helpful for postmenopausal patients, it would be desirable if bone mass was increased particularly in the local area of the hip and spine at a faster rate than for the rest of the patient's skeleton. Put another way, since bone mass has deteriorated most in the area of the hip and spine in many postmenopausal females, if needed, it would be desirable to increase the mineral accumulation in these areas at a faster rate in order to compensate for the greater loss.

It is, therefore, a primary objective of the present invention to provide a method of treatment of postmenopausal osteoporosis which not only overall increases patient bone mass but increases bone mass in a manner that is particularly suitable for patient treatment where the loss has been significant in the hip and spine.

Another objective of the present invention is to provide a method of treatment of postmenopausal osteoporosis which can be used in combination with the method of my earlier patents using $GRF(1-44)-NH_2$ or a biologically acceptable analog thereof to synergistically increase bone mass in the hip and spine area.

Another objective of the present invention is to provide a method of successfully administering $GRF(1-44)-NH_2$ or biologically acceptable analogs thereof concurrently with parathyroid hormone $(PTH(1-34)-NH_2)$ or biologically acceptable analogs thereof, with the combination enhancing the effect in reversing bone mass loss in postmenopausal patients beyond that which can be achieved by administering either individually.

A still further objective of the present invention is to provide a nasal insufflation composition which can be used in a combined treatment protocol for a synergistic treatment of osteoporosis.

The method and means of accomplishing each of the above objectives, as well as others, will become apparent from the description of the invention which follows hereinafter.

It goes without saying that certain modifications to the growth hormone releasing factor itself, or to the composition containing the same, may be made without department from the spirit or scope of the present invention. Put another way, modifications both in the formula to provide some related analogs of the growth release factor, and in the composition to provide either other forms of administration, or other pharmaceutically acceptable related compositions may be made. These modifications are included in the scope of this invention.

SUMMARY OF THE INVENTION

Osteoporosis, preferably postmenopausal osteoporosis, is treated by administering on a periodic but regular basis to a patient a growth hormone releasing effective amount of GRF(1-44)-NH$_2$, or a biologically acceptable analog thereof, and concurrently administering parathyroid hormone (PTH) or a biologically acceptable analog thereof, and monitoring the skeletal formation. The administration continues until the bone mass increases and the patient's calcium balance becomes positive, indicating mineral accumulation in the skeleton.

DETAILED DESCRIPTION OF THE INVENTION

In osteoporosis, growth plates epiphyses have closed in these adults and in the case of postmenopausal osteoporosis, as heretofore explained, there is a loss of bone in the skeleton leaving what might be described as "hollow bones." These hollow ones are highly susceptible to fracture. The treatment process of my earlier invention takes advantage of the fact that the adult skeleton of low mass will respond to growth hormone by reexpanding its mass. Growth plates are not involved, and therefore, the treatment should last for several years, perhaps with repeated courses of treatment if bone loss again resumes after treatment is stopped. The purpose of the treatment is to restore lost bone to the skeleton, thereby preventing fractures.

GRF(1-44)-NH$_2$ is an attractive molecule for treatment of postmenopausal osteoporosis because the molecule is relatively small and simple, and therefore, can be effective when given by nasal insufflation, using an appropriate vehicle. It is small enough to be absorbed across the nasal mucous membrane and reach the circulation intact in relatively high concentration, Since it is necessary to give the growth hormone releasing factor repeatedly over a long period of time, this route of administration, i.e., nasal insufflation, is preferred and has great convenience and comfort over parenteral administration by techniques such as intramuscular, subcutaneous or intravenous administration which require repeated injections with a needle and syringe. It is, however, possible that such parenteral means of dosage administration may be used, although less preferred. It is also conceivable that growth hormone releasing factor may be given by pill or capsule, but to date no such pills or capsules have yet been developed. Nasal insufflation is preferred because of its rapid absorption into the systemic system of the body.

The dosage level for GRF will vary, depending upon the age, weight and size of the patient, but typically satisfactory results may be obtained when administered at levels of from 1 ug/day up to about 100 ug/day. A preferred dosage level is from 1 ug/day to about 5 ug/day. Shortly after administration, the patient may observe a flushed feeling, but this dissipates quickly.

Administration should continue until clinical evaluation reveals that bone mass has increased, preferably to within the range of from about 10 percent increase to about 15 percent increase. For administration by nasal insufflation, insufflation should occur from about 1 to about 6 times daily.

It has been demonstrated in known literature that patients treated in clinical trials with PTH do show an increase in bone mass in some parts of the skeleton, see Canalis, et al., *Journal of Clinical Investigation*, 83:60-65 (1989); Reeve, et al., *British Medical Journal*, 1:1340-1344, 1980; and McCarthy, et al., *Endocrinology*, 124:1247-1253, 1989.

While it has been demonstrated that PTH can be used in a manner which when properly administered shows some evidence of bone mass increase for the skeleton, it also has been demonstrated that there are certain undesirable effects from use of PTH. In particular, PTH has the unusual effect of causing decrease of bone mass in certain long bones such as the femur, tibia, humor, and the radius, while at the same time causing increase of bone mass in the hip and the spine. Thus, the net effect of PTH or its biological analogs when administered is a sort of "robbing Peter to pay Paul" effect.

It has now been discovered, however, that if parathyroid hormone (PTH) is administered in conjunction with GRF, that the systemic effect of hormone induced release by the growth hormone releasing factor, in some manner not known to the applicant, minimizes and/or eliminates the normal undesirable effect of parathyroid hormone of causing decrease in bone mass in long bones, while having no effect on the desirable (PTH) property of increasing bone mass in the hip and spine. There is, therefore, a synergistic and desirable effect when human GRF is administered concurrently with human parathyroid hormone (PTH).

The improved method of using GRF for the treatment of osteoporosis does not change the schedule of administration of GRF outlined in my earlier two patents mentioned above, but does add a schedule of administration of PTH(1-34), or other biologically active analogs thereof, at a dose of from about 50 micrograms to about 200 micrograms twice daily, preferably by the subcutaneous route at the time of administration of GRF. This dose of PTH has been used for several purposes in humans and has been found to be very safe.

While the dosage of PTH has been described as from about 50 micrograms to about 200 micrograms twice daily, it should be understood that more may be used if desired. However, in human tests, it has been found that the activity of human PTH when administered as described seems to plateau at about 200 micrograms twice daily. There is, therefore, based on experience to date not any scientifically or medically sound reason for using excess amounts over and above those described herein. It is not to say, however, that larger doses may not be noneffective in the future. It is possible that they may.

There are many sources for human PTH from ethical pharmaceutical companies. For example, it can be obtained from Rorer Pharmaceuticals, and it can synthetically be produced if desired, even by use of recombinant technology.

The treatment here is for use of PTH in conjunction with GRF. It is possible a combined composition could be simultaneously administered, but so far the treatment protocol contemplated is administration of the doses from separate units but to the same patient. Each can be administered individually with the order being not critical. Generally, an efficient protocol would be administration of GRF first and then the PTH, since the GRF is known to have a systemic effect rather than local. This is the preferred order.

Human PTH, a polypeptide made up of 84 amino acids is secreted by the parathyroid gland normally in response to lowered serum ionized calcium. The entire function of the hormone is contained in the 1-34 amino acid sequence of the molecule. Its function is to help maintain serum ionized calcium levels within fairly narrow limits. While the foregoing description has primarily been with reference to naturally occuring human PTH(1-84)-NH$_2$ and the commonly available 1-34 amino acid sequence which is known to contain the entire function of the hormone, it should be noted that biologically active analogs thereof may also be used if available. It is contemplated that such analogs would be within the scope of the invention.

Similarly, with respect to growth hormone releasing factor GRF(1-44)-NH$_2$, it should be noted that biologically active analogs thereof may also be used. There are several analogs of GRF(-144)-NH$_2$ which have biological activity, but are somewhat less potent. It is contemplated that those analogs which are biologically active may also be used in the treatment process of the invention. They may be selected from the group consisting of GRF(1-44)-NH$_2$, GRF(-140)-OH, GRF(1-40)-NH$_2$, GRF(1-32)-NH$_2$, GRF(1-39)-NH$_2$, GRF(1-40)-Phe-NH$_2$, GRF(1-40)-Phe-OH, GRF(1-40)-Phe-Gin-NH$_2$, and GRF(1-27)-NH$_2$.

The following example is set forth to provide a sample protocol for administration of GRF(1-44)-NH$_2$ or its biologically active analogs in conjunction with human parathyroid hormone (PTH) or its biologically active analogs.

EXAMPLE

The patient protocol would be a white female past the age of menopause with low bone mass. The patient may or may not have factures at the time of treatment is undertaken. Necessarily, prior to the treatment, the patient must have a clinical evaluation ruling out other causes of low bone mass, with the diagnosis of osteoporosis being established by measurement of bone mass by current methods such as single photon absorptiometry, dual photon absorptiometry, or CT scanning of the spine.

Growth hormone releasing factor is administered by the preferred nasal insufflation route, at levels ranging from 1 to 6 times daily at a total dose of 5 ug/day. This treatment is continued for a period of from 2 to 5 years during which time bone mass measurements are repeated at intervals of from 6 to 12 months. Treatment should be continued until there is an increase in bone mass of from 10 percent to about 15 percent. Thereafter, the patient's bone mass is periodically checked, perhaps once per year, and treatment reinstated with similar doses with the indentical protocol if there is bone loss shown.

In conjunction with the previously described administration of GRF, the schedule of administration to the same patient of PTH(1-34) is followed at a dose of 200 micrograms, twice daily, by this subcutaneous route. When this is done, in comparison with patients for which this is not done, increase in bone skeletal mass in the hip and spine is noted without any expected loss of bone mass in the long bones. Thus, the overall increase in bone mass of 10 to 15 percent occurs in the areas where this is specially needed.

When in the above example a naturally occurring growth hormone releasing factor GRF(1-44)-NH$_2$ is replaced with biologically active analogs thereof, substantially similar results are obtained. In particular, the biologically active analogs of GRF(1-44)-NH$_2$ which can be used in the treatment process of this example are the following: GRF(1-40)-OH, GRF(1-40)-NH$_2$, GRF(1-32)-NH$_2$, GRF(1-39)-NH$_2$, GRF(1-40)-Phe-NH$_2$, GRF(1-40)-Phe-OH, GRF(1-40)-Phe-Gin-NH$_2$, and GRF(1-27)-NH$_2$.

When in the above example a naturally occurring parathyroid hormone PTH(1-84) is used, as opposed to the 1-34 amino acid sequence, similar results are observed.

What is claimed is:

1. A method of treating osteoporosis, comprising administering to a patient an osteoporosis treating effective amount of human GRF(1-44)-NH$_2$ or a biologically active analog thereof, and concurrently administering to the same patient an osteoporosis treating effective amount of human PTH or a biologically active analog thereof.

2. The method of claim 1 wherein the amount of GRF(1-44)-NH$_2$ analog administered is from about 1 ug/day to about 100 ug/day.

3. The method of claim 2 wherein the amount administered is from about 1 ug/day to about 5 ug/day.

4. The method of claim 1 wherein said treatment continues until bone mass increases to within the range of from about 10 percent to about 15 percent.

5. The method of claim 1 wherein the method of administration of said GRF is nasal insufflation.

6. The method of claim 1 wherein the method of administration is parenteral.

7. The method of claim 1 wherein said osteoporosis is old age osteoporosis.

8. The method of claim 1 wherein said osteoporosis is postmenopausal osteoporosis.

9. The method of claim 5 wherein said nasal insufflation occurs from 1 to 6 times daily.

10. The method of claim 1 wherein the human PTH is (1-84)-NH$_2$.

11. The method of claim 1 wherein the human PTH is (1-34)-NH$_2$.

12. The method of claim 1 wherein the PTH is administered at a dose of from about 50 micrograms to about 200 micrograms at least twice daily.

13. The method of claim 12 wherein the PTH is administered subcutaneously.

14. A method of treating osteoporosis, comprising:
administering to a patient a small but skeletal mass increasing effective amount of human GRF(1-44)-NH$_2$ or a biologically active analog thereof selected from the group consisting of GRF(1-40)-OH, GRF(1-40)-NH$_2$, GRF(1-32)-NH$_2$, GRF(1-39)-NH$_2$, GRF(1-40)-Phe-NH$_2$, GRF(1-40)-Phe-OH, GRF(-140)-Phe-Gin-NH$_2$, and GRF(1-27)-NH$_2$; and
concurrently administering to the same patient a small but skeletal mass increasing effective amount of human PTH(1084) or PTH(1-34) or biologically active analogs thereof.

15. The method of claim 14 wherein the PTH is administered subcutaneously and the GRF is administered by nasal insufflation.

16. The method of claim 14 wherein both the GRF and the PTC are administered by nasal insufflation.

17. The method of claim 16 wherein the GRF is GRF(1-44)-NH$_2$ and the PTH is PTH(1-34)-NH$_2$.

* * * * *

UNITED STATES PATENT AND TRADEMARK OFFICE
CERTIFICATE OF CORRECTION

PATENT NO. : 5,164,368
DATED : November 17, 1992
INVENTOR(S) : Robert R. Recker

It is certified that error appears in the above-indentified patent and that said Letters Patent is hereby corrected as shown below:

Column 5, line 9, after "(1-84)" delete — -NH$_2$ —.

Abstract, line 6, after "(1-34)" delete — -NH$_2$ —.

Column 6, line 40, claim 10, delete — -NH$_2$ —.

Column 6, line 42, claim 11, delete — -NH$_2$ —.

Column 6, line 59, claim 14, delete "1084" and insert —1-84—.

Column 6, line 68, claim 17, line 2 delete the second occurrence of -NH$_2$

Signed and Sealed this

Thirteenth Day of September, 1994

Attest:

BRUCE LEHMAN

Attesting Officer

Commissioner of Patents and Trademarks